United States Patent [19]
Comin-DuMong

[11] Patent Number: 5,458,589
[45] Date of Patent: Oct. 17, 1995

[54] WITHDRAWAL STRING FOR A TAMPON

[76] Inventor: Shella Comin-DuMong, 1403 S. Jameson La., Santa Barbara, Calif. 93108

[21] Appl. No.: 236,700

[22] Filed: Apr. 28, 1994

Related U.S. Application Data

[63] Continuation of Ser. No. 980,579, Nov. 23, 1992, abandoned.

[51] Int. Cl.$^6$ ............................ A61F 13/15; A61F 13/20
[52] U.S. Cl. ............................ 604/358; 604/11; 604/904
[58] Field of Search .......................... 604/1–3, 11–18, 604/904, 358

[56] References Cited

U.S. PATENT DOCUMENTS

| | | | |
|---|---|---|---|
| 4,186,730 | 2/1980 | Bucalo | 128/769 |
| 4,232,673 | 11/1980 | Bucalo | 128/769 |
| 4,746,237 | 5/1988 | Sweere | 604/358 |
| 5,004,467 | 4/1991 | Hinzmann et al. | 604/904 |
| 5,006,116 | 4/1991 | Alikhan et al. | 604/365 |

*Primary Examiner*—Randall L. Green
*Assistant Examiner*—Dennis Ruhl
*Attorney, Agent, or Firm*—Michael G. Petit

[57] ABSTRACT

The present invention provides an improved tampon for preventing conduction of menstrual fluids from the vagina. The tampon comprises an absorbable pledget of the type well known in the art capable of absorbing menstrual discharge and a withdrawal string non-releasably attached to the pledget. The withdrawal string is a non-absorbing fiber that is non-wicking for aqueous liquids. The withdrawal string prevents the inadvertent wicking or conduction of exogenous fluids such as sea water into the vagina or of menstrual fluid from the vagina into absorbable undergarments.

1 Claim, 1 Drawing Sheet

WITHDRAWAL STRING FOR A TAMPON

CROSS REFERENCE TO RELATED APPLICATIONS

This is a continuation of application Ser. No. 07/980,579; filed Nov. 23, 1992 now abandoned.

BACKGROUND OF THE INVENTION

1. Field of the Invention

This invention relates to an improved tampon and, more specifically, to an improved non-wicking withdrawal string for a tampon.

2. Prior Art

Prior art tampons normally comprise a cylindrical pledget of a non-irritating, absorbable material such as cotton or rayon formed by compression into an easily insertable shape prior to use. A withdrawal string is typically attached to the pledget during construction to facilitate the removal of the tampon from the vagina following its use.

The absorbent characteristics of a particular tampon depend upon, among other things, the geometry of the pledget as well as its method of fabrication and the material thereof. Those tampons enjoying success in the marketplace permit the continual absorption of blood and other vaginal discharge even in the presence of clotting blood. Thus, modern tampons have a great capacity for absorption of blood. Unfortunately, the withdrawal string that is used to retrieve the tampon from the vagina is typically made of an absorbable or intertwined material which, when wetted such as by urine, perspiration or from swimming, serves as a wick to conduct discharge and blood from the vagina into the undergarment of the wearer. Thus, not only are tampons are changed more frequently, but undergarments are soiled and stained more regularly than would otherwise be the case in the absence of such conduction or wicking.

Surprisingly, the development of a non-wicking withdrawal string for use with a tampon has received no attention. Indeed, the problem of wicking of fluids into or out of the vagina by the withdrawal string has not been addressed in the art. As used herein, the term "wicking" refers to the physical transport of fluid into or out of the vagina by a drawstring. Commonly, cotton is used as a withdrawal string. Rayon, which is also frequently used for the tampon pledget itself, has also been recommended for use as a withdrawal string. Such strings, as mentioned above, suffer from an inescapable tendency to conduct, or wick, fluids. Since the withdrawal string extends from the pledget to the outside of the vagina, such conduction is undesirable.

Glassman, in U.S. Pat. No. 5,047,024, describes a withdrawal string that is double-stranded and of an unknown material. While no mention of the specific material is made, if the withdrawal string material is absorbable, it would wick fluid from the vagina. If it is not absorbable, the intertwined, double-stranded nature of the withdrawal string, would, by capillary action, also conduct fluid from the vagina to the exterior.

Hinzmann et al., in U.S. Pat. No. 5,004,467, describe a tampon comprising a cylindrical pledget and a withdrawal string. Hinzmann provides no characterization of the physical, chemical or mechanical properties of the material preferably comprising the withdrawal string. Walton et al., in U.S. Pat. No. 4,627,849, describe a tampon that utilizes an absorbent rayon withdrawal string. Such strings would conduct fluid from the vagina. U.S. Pat. Nos. 4,222,381 and 4,018,225 describe further embodiments of vaginal tampons employing withdrawal strings of unknown composition.

It is desirable to provide a tampon that has a withdrawal string that does not conduct fluids from the vagina. It is also desirable to provide a withdrawal string for a tampon which prevents "reverse wicking" of exogenous fluids into the vagina as may occur when the wearer engages in any water activity such as swimming, or in strenuous activities producing perspiration. "Reverse wicking" of exogenous fluids will saturate or "water log" the tampons, necessitating immediate change. The objectives are achieved by the improved drawstring of the present invention.

SUMMARY OF THE INVENTION

This invention is an improved tampon having a withdrawal string that does not conduct vaginal or menstrual discharge. The withdrawal string is preferably a single-stranded non-absorbable filament.

BRIEF DESCRIPTION OF THE PREFERRED EMBODIMENT

Figure 1:
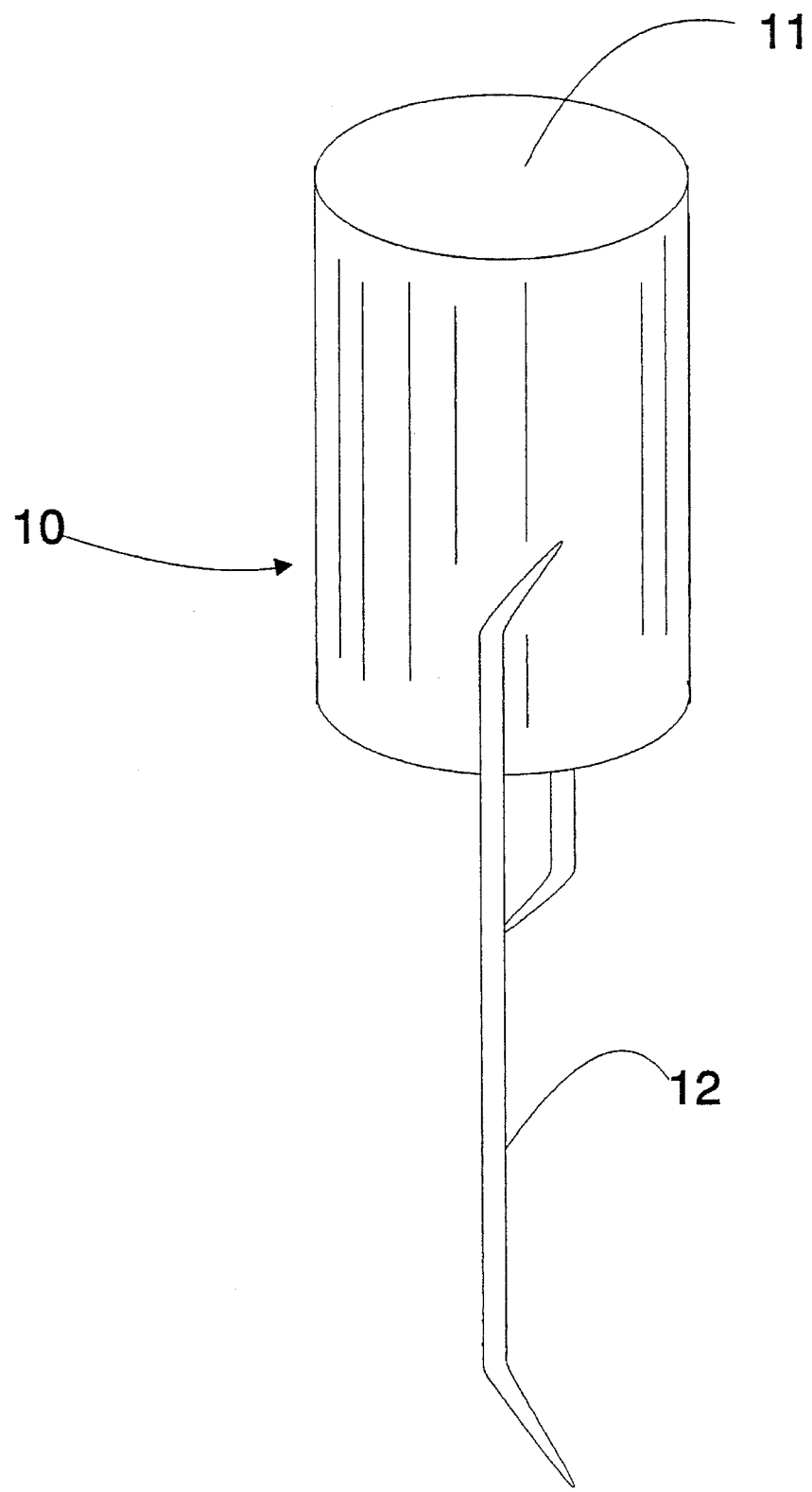
FIG. 1 shows a tampon comprising a pledget and withdrawal string.

A tampon, generally indicated at the numeral 10, consists of an absorbable, usually cylindrical or rectangular pledget 11 non-releasably attached to a withdrawal string 12. The withdrawal string may be attached to the pledget by a variety of means such as is well known in the prior art. Friese, for example, in U.S. Pat. No. 4,490,894 shows an apparatus for attaching a withdrawal string to a tampon.

The withdrawal string 12 comprises a hydrophobic monofilament such as dacron or siliconized dacron. The monofilamentous nature of the withdrawal string prevents the unwanted conduction of menstrual/vaginal fluids along the string by means of capillary action. The hydrophobic nature of the material itself prevents the conduction of menstrual/vaginal fluids to the exterior of the vagina by absorption and wicking action. Such a non-wicking drawstring will also prevent reverse wicking as mentioned earlier.

The above-described preferred embodiment provides a tampon which materially improves the performance of the pessary in preventing the condition of menstrual and/or vaginal discharge into undergarments during use. Additionally, it will prevent reverse wicking. The preferred embodiment is exemplary. It is within the scope of this invention to include any withdrawal string that is non-wicking to aqueous liquids such as menstrual discharge, urine, pool water, sea water, perspiration or other liquids and incapable of conducting such fluids along its length by capillary action. Suitable materials for the withdrawal string include monofilamentous organic polymers or an absorbent material such as cotton which has been coated with a hydrophobic layer.

What I claim is:

1. A tampon comprising an absorbent pledget with a withdrawal string having a fixed end attached to the pledget and a free end, said withdrawal string consisting of a single hydrophobic monofilament material having unitary construction wherein said withdrawal string is operable for preventing the wicking of aqueous liquids between said free end and fixed end thereof.

* * * * *